United States Patent [19]

Baker et al.

[11] Patent Number: 5,106,733
[45] Date of Patent: Apr. 21, 1992

[54] BOVINE GRANULOCYTE-MACROPHAGE COLONY STIMULATING FACTOR

[75] Inventors: Paul E. Baker, Bainbridge Island; Douglas P. Cerretti, Seattle; William R. Clevenger, Seattle; David J. Cosman, Seattle; Charles R. Maliszewski, Seattle, all of Wash.

[73] Assignee: Immunex Corporation, Seattle, Wash.

[21] Appl. No.: 355,870

[22] Filed: May 22, 1989

Related U.S. Application Data

[63] Continuation of Ser. No. 66,901, Jun. 25, 1987, abandoned.

[51] Int. Cl.$^5$ .................... C12P 21/02; C12N 15/27; C12N 15/00
[52] U.S. Cl. ............................ 435/69.5; 435/240.1; 435/243; 435/320.1; 536/27
[58] Field of Search ............... 435/68, 70, 172.3, 253, 435/255, 320, 69.1, 69.5; 536/27; 935/19, 20, 21, 2, 3

[56] References Cited

FOREIGN PATENT DOCUMENTS

WO85/04188  9/1985  PCT Int'l Appl. .

OTHER PUBLICATIONS

Cerretti et al., *Proc. Natl. Acad. Sci. U.S.A.*, 83:3223-3227 (1986).
Paul, William, Fundamental Virology, (1989), Raven Press, N.Y., p. 362.
Yang et al., *Cell*, vol. 47:3-10 (1986).
Cohen et al., *Nucleic Acids Research*, vol. 14:3641-3658 (1986).
Leonj et al., *Chem. Abst.*, vol. 112(19), No. 173547t, 1989, "Cloning and Expression of the CDNA for Bovine Granulocyte-Macrophage Colony-Stimulating Factor".
Picha et al., *Immunology*, vol. 57, pp. 131-136 "Bovine T Lymphocytes".
Cerretti et al., (1986), J. of Immunology, 136:4561-64.
Burgess et al., "Purification and Properties on Colony-Stimulating Factor from Mouse Lung-Conditioned Medium." *J. Biol. Chem.* 252:1998 (1977).
Sparrow et al., "Purification and Partial Amino Acid Sequence of Asialo Murine Granuloctye-Macrophage Colony Stimulating Factor" *Proc. Natl. Acad. Sci*, 82:292 (1985).
Gough et al., "Molecular Cloning of the cDNA Encoding a Murine Haematopoietic Growth Regulator, Granulocyte-Macrophage Colony Stimualting Factor." *Nature*, 309:763 (1984).
Gough et al., "Structure and Expression of the mRNA for Murine Granulocyte-Macrophage Colony Stimulating Factor." *EMBO Journal* 4:645-653 (1985).
Price et al., "Expression, Purification and Characterization of Recombinant Murine Granulocyte-Macrophage Colony-Stimulating Factor and Bovine Interleukin-2 from Yeast." *Gene* 55:287-293 (1987).
DeLarmarter et al., "Recombinant Murine GM-CSF from *E. coli* Has Biological Activity and is Neutralized by a Specific Antiserum." *EMBO Journal* 4:2575-2581 (1985).
Stanley et al., "The Structure and Expression of the Murine Genes Encoding Granulocyte-Macrophage Colony Stimulating Factor: Evidence for Utilisation of Alternative Promoters." *EMBO Journal* 4:2569-2573 (1985).
Gasson et al., "Purified Human Granulocyte-Macrophage Colony-Stimulating Factor: Direct Action on Neutrophils." *Science* 226:1339 (1984).

(List continued on next page.)

Primary Examiner—Richard A. Schwartz
Assistant Examiner—S. L. Nolan
Attorney, Agent, or Firm—Christopher L. Wight; Scott G. Hallquist

[57] ABSTRACT

Cloning and expression of DNA segments encoding bovine GM-CSF, and processes for producing recombinant bovine GM-CSF as a product of recombinant cell culture, are disclosed.

10 Claims, 2 Drawing Sheets

OTHER PUBLICATIONS

Lusis et al., "Translation of mRNA for Human Granulocyte-Macrophage Colony Stimulating Factor." *Nature* 298:75 (1982).

Lee et al., "Isolation of cDNA for a Human Granulocyte-Macrophage Colony-Stimulating Factor by Functional Expression in Mammalian Cells." *Proc. Natl. Acad. Sci.* 82:4360 (1985).

Tomonaga et al., "Biosynthetic (Recombinant) Human Granulocyte-Macrophage Colony-Stimulating Factor: Effect of Normal Bone Marrow and Leukemia Cell Lines." *Blood* 67:31 (1986).

Kaushansky et al., "Genomic Cloning, Characterization, and Multilineage Growth-Promoting Activity of Human Granulocyte-Macrophage Colony-Stimulating Factor." *Proc. Natl. Acad. Sci.* 83:3101 (1986).

Cantrell et al., "Cloning, Sequence, and Expression of a Human Granulocyte/Macrophage Colony-Stimulating Factor." *Proc. Natl. Acad. Sci.* 82:6250 (1985).

Wong et al., "Human GM-CSF: Molecular Cloning of the Complementary DNA and Purification of the Natural and Recombinant", *Science* 228:810 (1985).

Metcalf et al., "Biologic Properties in Vitro of a Recombinant Human Granulocyte-Macrophage Colony-Stimulating Factor." *Blood* 67:37 (1986).

Miyajima et al., "Expression of Murine and Human Granulocyte-Macrophage Colony-Stimulating Factors in *S. cerevisiae*: Mutagenesis of the Potential Glycosylation Sites." *EMBO Journal* 5:1193 (1986).

Miyatake et al., "Structure of the Chromosomal Gene for Granulocyte-Macrophage Colony Stimulating Factor: Comparison of the Mouse and Human Genes." *EMBO Journal* 4:2561 (1985).

Metcalf, "The Molecular Biology and Functions of the Granulocyte-Macrophage Colony-Stimulating Factors." *Blood* 67:257 (1986).

FIGURE 1: Bovine GM-CSF cDNA

| | | | | | |
|---|---|---|---|---|---|
| AGTCCTCAAG | AGGATGTGGC | TGCAGAACCT | GCTTCTCCTG | GGCACTGTGG | 50 |
| TCTGCAGCTT | CTCCGCACCT | ACTCGCCCAC | CCAACACTGC | CACCCGGCCC | 100 |
| TGGCAGCATG | TGGATGCCAT | CAAGGAGGCC | CTGAGCCTTC | TGAACCACAG | 150 |
| CAGTGACACT | GATGCTGTGA | TGAATGACAC | AGAAGTCGTC | TCTGAAAAGT | 200 |
| TTGACTCCCA | GGAACCAACG | TGCCTGCAGA | CTCGCCTGAA | GCTGTACAAG | 250 |
| AACGGCCTGC | AGGGCAGCCT | CACTAGTCTC | ATGGGCTCCT | TGACCATGAT | 300 |
| GGCCACCCAC | TACGAGAAAC | ACTGCCCACC | CACCCCGGAA | ACTTCCTGTG | 350 |
| GAACCCAGTT | TATCAGCTTC | AAAAATTTCA | AGAGGACCT | GAAGGAGTTC | 400 |
| CTTTTTATCA | TTCCCTTTGA | CTGCTGGGAA | CCAGCCCAGA | AGTGAAGCAG | 450 |
| GCCAAACCAG | CCAGAAGTGG | AAGCTTACCT | CACAGATCGC | TGCCCTCCTA | 500 |
| CCCACAAAGA | GCCAAACAAA | ACTCAGGATC | TTCACACTGG | AGGGACCACA | 550 |
| GGGAGGGCCA | GAGCTGTAGG | GGGCCGCTGG | CTTGTTCAGG | GCCATGTTGA | 600 |
| CCCTGATACA | GGTGTGGCAG | GGGAAACGGG | AAATGTTTTA | CACTGGCAGG | 650 |
| GATCAGCAAT | ATTTATTTAT | ATATTTATGT | ATTTAATAT | TTATTTATTT | 700 |
| ATTTATTTAA | ACTCATACCC | CATATTTATT | CAAGATGTTT | TTCTATAATA | 750 |
| ATAAATTATT | CAAAGTCAAA | AAAAAAAAA | AAA | | 783 |

FIGURE 2: Coding and Derived Amino Acid Sequence of bGM-CSF

| | | | | | | | | | | | | | | | |
|---|---|---|---|---|---|---|---|---|---|---|---|---|---|---|---|
| ATG | TGG | CTG | CAG | AAC | CTG | CTT | CTC | CTG | GGC | ACT | GTG | GTC | TGC | AGC | 45 |
| Met | Trp | Leu | Gln | Asn | Leu | Leu | Leu | Leu | Gly | Thr | Val | Val | Cys | Ser | 15 |
| | | ↓ | | | | | | | | | | | | | |
| TTC | TCC | GCA | CCT | ACT | CGC | CCA | CCC | AAC | ACT | GCC | ACC | CGG | CCC | TGG | 90 |
| Phe | Ser | Ala | Pro | Thr | Arg | Pro | Pro | Asn | Thr | Ala | Thr | Arg | Pro | Trp | 30 |
| CAG | CAT | GTG | GAT | GCC | ATC | AAG | GAG | GCC | CTG | AGC | CTT | CTG | AAC | CAC | 135 |
| Gln | His | Val | Asp | Ala | Ile | Lys | Glu | Ala | Leu | Ser | Leu | Leu | Asn | His | 45 |
| AGC | AGT | GAC | ACT | GAT | GCT | GTG | ATG | AAT | GAC | ACA | GAA | GTC | GTC | TCT | 180 |
| Ser | Ser | Asp | Thr | Asp | Ala | Val | Met | Asn | Asp | Thr | Glu | Val | Val | Ser | 60 |
| GAA | AAG | TTT | GAC | TCC | CAG | GAA | CCA | ACG | TGC | CTG | CAG | ACT | CGC | CTG | 225 |
| Glu | Lys | Phe | Asp | Ser | Gln | Glu | Pro | Thr | Cys | Leu | Gln | Thr | Arg | Leu | 75 |
| AAG | CTG | TAC | AAG | AAC | GGC | CTG | CAG | GGC | AGC | CTC | ACT | AGT | CTC | ATG | 270 |
| Lys | Leu | Tyr | Lys | Asn | Gly | Leu | Gln | Gly | Ser | Leu | Thr | Ser | Leu | Met | 90 |
| GGC | TCC | TTG | ACC | ATG | ATG | GCC | ACC | CAC | TAC | GAG | AAA | CAC | TGC | CCA | 315 |
| Gly | Ser | Leu | Thr | Met | Met | Ala | Thr | His | Tyr | Glu | Lys | His | Cys | Pro | 105 |
| CCC | ACC | CCG | GAA | ACT | TCC | TGT | GGA | ACC | CAG | TTT | ATC | AGC | TTC | AAA | 360 |
| Pro | Thr | Pro | Glu | Thr | Ser | Cys | Gly | Thr | Gln | Phe | Ile | Ser | Phe | Lys | 120 |
| AAT | TTC | AAA | GAG | GAC | CTG | AAG | GAG | TTC | CTT | TTT | ATC | ATT | CCC | TTT | 405 |
| Asn | Phe | Lys | Glu | Asp | Leu | Lys | Glu | Phe | Leu | Phe | Ile | Ile | Pro | Phe | 135 |
| GAC | TGC | TGG | GAA | CCA | GCC | CAG | AAG | TGA | | | | | | | 429 |
| Asp | Cys | Trp | Glu | Pro | Ala | Gln | Lys | End | | | | | | | 143 |

BOVINE GRANULOCYTE-MACROPHAGE COLONY STIMULATING FACTOR

This application is a continuation of application Ser. No. 07/066,901, filed June 25, 1987, now abandoned.

BACKGROUND OF THE INVENTION

The present invention relates generally to mammalian cytokines, and particularly to cloning and expression of a biologically active recombinant bovine GM-CSF capable of inducing hematopoietic cell development.

Granulocyte-macrophage colony stimulating factor (GM-CSF) refers to a protein capable of inducing development of granulocyte and macrophage precursor cells from bone marrow progenitors. GM-CSF also appears to regulate the activity of mature, differentiated granulocytes and macrophages. Murine GM-CSF was initially identified as a 23 kilodalton protein present in preparations obtained from endotoxin-conditioned mouse lung which stimulated development of granulocyte and macrophage precursor colonies in soft agar cultures. See Burgess et al., *J. Biol. Chem.* 252:1998 (1977). Human GM-CSF activity was partially purified from placental conditioned medium by Nicola et al., *Blood* 54:614 (1979). Human GM-CSF has also been identified in cultures of the human T-lymphoblast cell line Mo, and shown to modulate the activities of mature neutrophilic granulocytes by Gasson et al., *Science* 226:1339 (1984). Cloning and expression of recombinant human GM-CSF from various sources has been reported by Cantrell et al., *Proc. Natl. Acad. Sci. USA* 82:6250 (1985); Wong et al., *Science* 228:810 (1985); and Lee et al., *Proc. Natl. Acad. Sci. USA* 82:4360 (1985). Cantrell et al. isolated human GM-CSF sequences from cDNA libraries prepared from the HUT-102 cell line. The isolated human sequences were shown to direct synthesis of a biologically active GM-CSF using a yeast expression system.

In view of its potential as a therapeutic agent for treating various cytopenias, and its apparent effect upon mature granulocytes and macrophages, there is interest in bovine GM-CSF (bGM-CSF) in veterinary medicine. Therapeutic compositions comprising biologically active recombinant bGM-CSF or active homologues could be employed to augment immune responsiveness to infectious pathogens, or to assist in reconstituting normal blood cell populations following viral infection or other conditions resulting in hematopoietic cell suppression.

SUMMARY OF THE INVENTION

The present invention provides recombinant bovine GM-CSF proteins and DNA segments consisting essentially of a single open reading frame nucleotide sequence encoding bovine GM-CSF. Preferably, such segments are provided in the form of a gene which is capable of being expressed in a recombinant transcriptional unit comprising regulatory elements derived from a microbial or viral operon. The present invention also provides recombinant expression vectors comprising the DNA segments, microbial expression systems comprising the recombinant expression vectors, and processes for making the proteins using the microbial expression systems.

BRIEF DESCRIPTION OF THE FIGURES

FIG. 1 illustrates the nucleotide sequence of a cDNA clone encoding bGM-CSF which was isolated using a probe derived from human GM-CSF cDNA. Initiation and termination codons of the bGM-CSF open reading frame are underlined.

FIG. 2 indicates the nucleotide sequence and derived amino acid sequence of the coding region of the cDNA clone of FIG. 1. The full-length translation product, including a putative hydrophobic signal peptide, is encoded by the sequence beginning at nucleotide 1 and ending at nucleotide 429. The sequence encoding the mature protein begins at nucleotide 52 (indicated by an arrow), the first nucleotide of the codon corresponding to alanine 18 in FIG. 2.

DETAILED DESCRIPTION OF THE INVENTION

A DNA segment encoding bGM-CSF was isolated from a cDNA library prepared by reverse transcription of polyadenylated RNA isolated from an interleukin-2 dependent bovine T-lymphocyte cell line, BT2, first described by Picha and Baker, *Immunol.* 57:131 (1985). A cDNA fragment corresponding to the coding sequence of human GM-CSF and including additional 5' and 3' flanking sequences was employed to screen the library by DNA hybridization techniques. Clones which hybridized to the probe were analyzed by restriction endonuclease cleavage, agarose gel electrophoresis, and additional hybridization experiments ("Southern blots") involving the electrophoresed fragments. After isolating several clones which hybridized to the human cDNA probe, the hybridizing segment of one bGM-CSF clone was subcloned and sequenced by conventional techniques. A cDNA sequence comprising the coding regions of the bGM-CSF gene was inserted into a mammalian high expression vector under regulatory control of an SV40 viral promoter, and the resulting construct used to transfect monkey COS-7 cells. The plasmid construct directed synthesis of a 22 kilodalton protein with GM-CSF activity in cultures of nonadherent bovine bone marrow cells. A yeast vector was also constructed, which was capable of expressing a secreted fusion protein exhibiting bGM-CSF biological activity.

Alternatively, expression vectors can be assembled comprising synthetic or cDNA-derived DNA fragments encoding bGM-CSF or bioequivalent homologues operably linked to inducible elements derived from genes of bacteria, yeast, bacteriophage, or viruses. Following transformation or transfection of appropriate cell lines, such vectors can be induced to express recombinant protein.

In nucleic acid embodiments, the present invention provides DNA segments consisting essentially of a single open reading frame nucleotide sequence encoding bovine GM-CSF. As previously noted, such DNA segments preferably consist essentially of a gene encoding bGM-CSF which is capable of being expressed in a recombinant transcriptional unit comprising inducible regulatory elements derived from a microbial or viral operon. In preferred aspects, the DNA segments comprise at least one, but optionally more than one, sequence component derived from a cDNA sequence or copy thereof. Such sequences may be linked or flanked by DNA sequences prepared by assembly of synthetic oligonucleotides. Exemplary sequences include those substantially homologous to the nucleotide sequence depicted in FIG. 2, but encoding a polypeptide having as its amino terminus the alanine residue indicated at position 18. Optionally, the coding sequences may include codons encoding one or more additional amino acids located at the N-terminus, for example an N-terminal ATG codon specifying methionine linked in reading frame with the nucleotide sequence. Due to code degeneracy, there can be considerable variation in nucleotide sequences encoding the same amino acid sequence; one exemplary DNA embodiment is that corresponding to the sequence of nucleotides 52-429 of FIG. 2. The present invention also provides recombinant cloning or expression vectors comprising any of the foregoing DNA segments. The vectors may include regulatory elements such as those described in greater detail below.

In process aspects, the present invention provides processes for preparing purified rbGM-CSF or bioequivalent homologues thereof, comprising culturing suitable host/vector systems to express the recombinant translation products of the synthetic genes of the present invention.

In protein embodiments, the present invention provides substantially homogeneous recombinant bGM-CSF polypeptides free of contaminating endogenous materials and optionally, without associated native-pattern glycosylation. Such proteins include, as one embodiment, N-terminal methionyl bGM-CSF. An additional embodiment is a bovine GM-CSF protein expressed as a fusion protein with a polypeptide leader comprising the sequence Asp-Tyr-Lys-(Asp$_4$)-Lys.

In composition and method-of-use aspects, the present invention provides veterinary therapeutic compositions comprising an effective amount of any of the bGM-CSF proteins of the invention and a suitable diluent or carrier, and methods for stimulating hematopoietic cell development or modulating or augmenting immune response in a bovine mammal, comprising administering an effective amount of any of the foregoing compositions. Use in conjunction or admixture with other bovine lymphokines, e.g., bIL-1α or bIL-1β, is also contemplated.

Definitions

"Bovine granulocyte-macrophage colony stimulating factor" and "bGM-CSF" refer to a bovine endogenous secretory protein which is capable of inducing hematopoietic cell development and activating mature granulocytes and macrophages. As used throughout the specification, the term "mature bGM-CSF" means a protein having bGM-CSF biological activity and an amino acid sequence which is substantially homologous to the polypeptide sequence illustrated in FIG. 2, beginning with amino acid 18 (alanine) and ending with amino acid 143 (lysine). The predicted molecular weight of the protein corresponding to the sequence depicted in FIG. 1 is 16,200 daltons, exclusive of any glycosylation.

"Substantially homologous," which can refer both to nucleic acid and amino acid sequences, means that a particular subject sequence, for example, a mutant sequence, varies from a reference sequence by one or more substitutions, deletions, or additions, the net effect of which does not result in an adverse functional dissimilarity between reference and subject sequences. For purposes of the present invention, sequences having greater than 90 percent homology, equivalent biological activity, and equivalent expression characteristics are considered substantially homologous. For purposes of determining homology, truncation of the mature sequence should be disregarded. Sequences having lesser degrees of homology, comparable bioactivity, and equivalent expression characteristics are considered equivalents.

"Recombinant," as used herein, means that a protein is derived from recombinant (e.g., microbial or mammalian) expression systems. "rbGM-CSF" means recombinant bGM-CSF. "Microbial" refers to recombinant proteins made in bacterial or fungal (e.g., yeast) expression systems. As a product, "recombinant microbial" defines a bovine protein essentially free of native endogenous substances and unaccompanied by associated native glycosylation. Protein expressed in most bacterial cultures, e.g., E. coli, will be free of glycan; protein expressed in yeast will have a glycosylation pattern different from that expressed in mammalian cells.

"DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, using a cloning vector. Such segments are provided in the form of an open reading frame uninterrupted by internal nontranslated sequences, or introns, which are typically present in eukaryotic genes. Sequences of non-translated DNA may be present downstream from the open reading frame, where the same do not interfere with manipulation or expression of the coding regions. "Nucleotide sequence" refers to a heteropolymer of deoxyribonucleotides. Generally, DNA segments encoding the proteins provided by this invention are assembled from cDNA fragments and short oligonucleotide linkers, or from a series of oligonucleotides, to provide a synthetic gene which is capable of being expressed in a recombinant transcriptional unit comprising regulatory elements derived from a microbial or viral operon.

"Recombinant expression vector" refers to a plasmid comprising a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences. Structural units intended for use in yeast expression systems preferably include a leader sequence enabling extracellular secretion of translated protein by a host cell. Alternatively, where recombinant protein is expressed without a leader or transport sequence, it may include an N-terminal methionine residue. This residue may or may not be subsequently cleaved from the expressed recombinant protein to provide a final product.

"Recombinant expression system" means a substantially homogeneous monoculture of suitable host microorganisms, for example, bacteria such as E. coli or yeast such as S. cerevisiae, which have stably integrated a recombinant transcriptional unit into chromosomal DNA or carry the recombinant transcriptional unit as a component of a resident plasmid. Generally, cells constituting the system are the progeny of a single ancestral transformant. Recombinant expression systems as defined herein will express heterologous protein upon induction of the regulatory elements linked to the DNA segment or synthetic gene to be expressed.

Assay for bGM-CSF Biological Activity

Human or bovine bone marrow cells can be used in assays to detect bGM-CSF biological activity; however, bovine marrow is preferred due to greater sensitivity. The assay is conducted as described below.

1-2 g comminuted bone marrow (BM) tissue is suspended in 3-7 ml phosphate buffered saline (PBS; 0.02M sodium phosphate, 1.2M NaCl, pH 7.2) centrifuged, and resuspended to three times the original volume in fresh PBS, and 8 ml of the resulting suspension is layered on top of 5 ml of 54% Percoll/PBS in 15 ml centrifuge tubes. Tubes are spun at 1500 rpm for 20 min. Cells at the interface are removed and washed once in PBS by centrifugation. Pelleted cells are resuspended in α-Minimal Essential Medium (α-MEM, Gibco) without serum to a concentration of $2 \times 10^6$ cells/ml and 30 ml incubated for 2 hrs at 37° C. in 5% $CO_2$ in T75 culture flasks (Falcon Plastics, Oxnard CA, USA). Nonadherent cells are removed by gentle aspiration, washed in warm medium, and adjusted to a cell density of $1.25 \times 10^5$ cells/ml in α-MEM containing 15% fetal bovine serum.

Serial 3-fold dilutions of sample are made in 96-well tissue culture-treated microtiter plates, so that the final volume of each well is 50 μl. Thereafter, 50 μl of the BM cell suspension is also added to each well. Plates are incubated for 96 hours, at which time each well is pulsed with 25 μl of medium containing 80 μCi/ml [$^3$H]-thymidine (80 Ci/mM, New England Nuclear NET-0277) for an additional 5 hours. The contents of each well are harvested onto glass fiber strips using a multiple automated sample harvester and radionuclide incorporation is assessed by liquid scintillation counting. Units of activity are expressed as the inverse of the dilution which yields 50% of the maximum value measured for incorporated radiolabel in a particular assay.

Protein and Endotoxin Assays

Protein concentrations can be determined by any suitable method. However, the Bio-Rad total protein assay (Bio-Rad Laboratories, Richmond, Calif., USA) is preferred. Endotoxin levels in protein compositions are conveniently assayed using a commercial kit available from Whittaker Bioproducts, Walkersville, Md., U.S.A., (Quantitative Chromogenic LAL QCL-1000) or its equivalent. This method uses a modified Limulus amebocyte lysate and synthetic color-producing substrate to detect endotoxin chromogenically. Purified recombinant protein is tested for presence of endotoxin at multiple dilutions. The assay is preferably performed shortly following completion of purification and prior to storage at −70° C. To minimize the possibility of bacterial contamination during the purification process itself, sterile buffers should be employed.

The Native bGM-CSF Sequence

The nucleotide sequence of a cDNA clone isolated from a bovine BT2 cell library is set forth in FIG. 1. The open reading frame and corresponding amino acid sequence of bGM-CSF are illustrated in FIG. 2. In FIG. 2, nucleotides and amino acids are numbered beginning with the initiator methionine of the bGM-CSF precursor, which includes a putative 17 amino acid hydrophobic signal peptide. As defined herein, the mature sequence begins with a GCA codon specifying the alanine residue indicated by an arrow at residue 18. The predicted amino acid sequence of bGM-CSF includes an Asn-His-Ser sequence at amino acid residues 44-46 and an Asn-Asp-Thr sequence at residues 54-56 which provide potential N-linked glycosylation sites.

A recombinant DNA segment encoding the amino acid sequence of bGM-CSF can be obtained by screening of appropriate cDNA libraries using appropriate probes, or by assembly of artificially synthesized oligonucleotides.

Construction of expression vectors

Mature bGM-CSF can be expressed in mammalian cells, yeast, bacteria, or other cells under the control of appropriate promoters. Cell-free translation systems could also be employed to produce bGM-CSF using RNAs derived from the DNA constructs of the present invention. Appropriate cloning and expression vectors for use with bacterial, fungal, and yeast hosts are described by Pouwels, et al., *Cloning Vectors: A Laboratory Manual*, (Elsevier, N.Y., 1985), the relevant disclosure of which is hereby incorporated by reference.

Yeast systems, preferably employing Saccharomyces species such as *S. cerevisiae*, can be employed for expression of the recombinant proteins of this invention. Yeast of other genera, for example, Pichia or Kluyveromyces, have also been employed as production strains for recombinant proteins.

Generally, useful yeast vectors will include origins of replication and selectable markers permitting transformation of both yeast and *E. coli*, e.g., the ampicillin resistance gene of *E. coli* and *S. cerevisiae* TRP1 gene, and a promoter derived from a highly-expressed yeast gene to induce transcription of a downstream structural sequence. Such promoters can be derived from yeast operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the extracellular medium. Optionally, the heterologous sequence can encode a fusion protein including an N-terminal identification peptide (e.g., Asp-Tyr-Lys-(Asp)$_4$-Lys) or other sequence imparting desired characteristics, e.g., stabilization or simplified purfication of expressed recombinant product.

Useful yeast vectors can be assembled using DNA sequences from pBR322 for selection and replication in *E. coli* (Ap$^r$ gene and origin of replication) and yeast DNA sequences including a glucose-repressible alcohol dehydrogenase 2 (ADH2) promoter. The ADH2 promoter has been described by Russell et al., *J. Biol. Chem.* 258:2674 (1982) and Beier et al., *Nature* 300:724 (1982). Such vectors may also include a yeast TRP1 gene as a selectable marker and the yeast 2μ origin of replication. A yeast leader sequence, for example, the α-factor leader which directs secretion of heterologous proteins from a yeast host, can be inserted between the promoter and translation initiation sequence and in phase with the structural gene to be expressed. See Kurjan et al., *Cell* 30:933 (1982) and Bitter et al., *Proc. Natl. Acad. Sci. USA* 81:5330 (1984). The leader sequence may be modified to contain, near its 3′ end, one or more useful restriction sites to facilitate fusion of the leader sequence to foreign genes.

Suitable yeast transformation protocols are known to those of skill in the art; an exemplary technique is described by Hinnen, et al., *Proc. Natl. Acad. Sci. USA* 75:1929 (1978), selecting for Trp+ transformants in a selective medium consisting of 0.67% yeast nitrogen base, 0.5% casamino acids, 2% glucose, 10 µg/ml adenine and 20 µg/ml uracil.

Host strains transformed by vectors comprising the ADH2 promoter are grown for expression in a rich medium consisting of 1% yeast extract, 2% peptone, and 1% glucose supplemented with 80 µg/ml adenine and 80 µg/ml uracil. Derepression of the ADH2 promoter occurs upon exhaustion of medium glucose. Crude yeast supernatants are harvested by filtration and frozen or held at 4° C. prior to further purification.

Useful expression vectors for bacterial use are constructed by inserting a structural DNA sequence encoding bGM-CSF together with suitable translation initiation and termination signals in operable reading phase with a functional promoter. The vector will comprise one or more phenotypic selectable markers and an origin of replication to ensure amplification within the host. Suitable prokaryotic hosts for transformation include *E. coli*, *Bacillus subtilis*, *Salmonella typhimurium*, and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, WI, USA). These pBR322 "backbone" sections are combined with an appropriate promoter and the structural sequence to be expressed.

A particularly useful bacterial expression system employs the phage λ $P_L$ promoter and cI857ts thermolabile repressor. Plasmid vectors available from the American Type Culture Collection which incorporate derivatives of the λ $P_L$ promoter include plasmid pHUB2, resident in *E. coli* strain JMB9 (ATCC 37092) and pPLc28, resident in *E. coli* RR1 (ATCC 53082). Other useful promoters for expression in *E. coli* include the T7 RNA polymerase promoter described by Studier et al., *J. Mol. Biol.* 189:113 (1986), the lacZ promoter described by Lauer, *J. Mol. Appl. Genet.* 1:139–147 (1981) and available as ATCC 37121, and the tac promoter described by Maniatis, *Molecular Cloning: A Laboratory Manual* (Cold Spring Harbor Laboratory, 1982, p 412) and available as ATCC 37138.

Following transformation of a suitable host strain and growth of the host strain to an appropriate cell density, the selected promoter is derepressed by appropriate means (e.g., temperature shift or chemical induction) and cells cultured for an additional period. Cells are typically harvested by centrifugation, disrupted by physical or chemical means, and the resulting crude extract retained for further purification. Cells are grown, for example, in a 10 liter fermenter employing conditions of maximum aeration and vigorous agitation. An antifoaming agent (Antifoam A) is preferably employed. Cultures are grown at 30° C. in the superinduction medium disclosed by Mott et al., *Proc. Natl. Acad. Sci. USA* 82:88 (1985), optionally including antibiotics, derepressed at a cell density corresponding to $A_{600}$=0-.4–0.5 by elevating the temperature to 42° C., and harvested from 2–20, preferably 3–6, hours after the upward temperature shift. The cell mass is initially concentrated by filtration or other means, then centrifuged at 10,000 x g for 10 minutes at 4° C. followed by rapidly freezing the cell pellet.

Various mammalian cell culture systems can also be employed to express recombinant protein. Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, HeLa and BHK cell lines. Mammalian expression vectors may comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements. Additional details regarding the use of a mammalian high expression vector to produce a recombinant bGM-CSF are provided in Example 1, below.

Protein Purification

Recombinant protein produced in bacterial culture is usually isolated by initial extraction from cell pellets, followed by one or more salting-out, aqueous ion exchange or size exclusion chromatography steps. Finally, high performance liquid chromatography (HPLC) can be employed for final purification steps. Microbial cells employed in expression of rbGM-CSF can be disrupted by any convenient method, including freeze-thaw cycling, sonication, mechanical disruption, or use of cell lysing agents.

Fermentation of yeast which express bGM-CSF as a secreted protein greatly simplifies purification. Secreted recombinant protein resulting from a large-scale fermentation can be purified by methods analogous to those disclosed by Urdal et al., *J. Chromatog.* 296:171 (1984). This reference describes two sequential, reversed-phase HPLC steps for purification of recombinant human GM-CSF on a preparative HPLC column.

This approach can be implemented as follows. Yeast broth containing rbGM-CSF is first filtered through a 0.45µ filter and pumped, at a flow rate of 100 ml/min, onto a 5 cm×30 cm column packed with 15–20µ C-4 reversed phase silica (Vydac, the Separations Group, Hesperia, CA, USA). The column is equilibrated in 0.1% trifluoroacetic acid in water (Solvent A) prior to the application of the yeast broth and flushed with this solvent following application of broth to the column until the optical absorbance of the effluent approaches baseline values. At this time, a gradient of 0.1% trifluoroacetic acid in acetonitrile (Solvent B) is established that leads from 0% to 100% Solvent B at a rate of change of 2% per minute and at a flow rate of 100 ml/min. After initiation of the gradient, one minute fractions are collected and aliquots of the fractions analyzed for protein content by polyacrylamide gel electrophoresis and fluorescamine protein determination, and for bGM-CSF activity using an appropriate assay. Fractions containing bGM-CSF from this run are then pooled and diluted with 2 volumes of 0.9M acetic acid, 0.2M pyridine, pH 4.0. The diluted pool is then pumped onto a second 5 cm×30 cm column packed with 15-20μ silica (Vydac) that has been equilibrated in 75% Solvent A2 (0.9M acetic acid, 0.2M pyridine, pH 4.0) and 25% Solvent B2 (60% n-propanol in 0.9M acetic acid, 0.2M pyridine, pH 4.5). Following application of the material, the column is flushed with additional equilibration solvent and then a gradient leading from 25% to 100% Solvent B2 is established at a rate of change of 1% solvent B2 per minute in order to elute rbGM-CSF from the column.

Administration of bGM-CSF

In use, purified bovine GM-CSF is administered to a mammal for treatment in a manner appropriate to the indication. Thus, for example, bGM-CSF administered as a stimulator of hematopoiesis or modulator of immune effector cell function can be given by bolus injection, continuous infusion, sustained release from implants, or other suitable technique. Typically, bGM-CSF will be administered in the form of a composition comprising purified protein in conjunction with physiologically acceptable carriers, excipients or diluents. Neutral buffered saline or saline mixed with conspecific serum albumin are exemplary appropriate diluents. Preferably, product is formulated as a lyophilizate using sucrose as diluent. Appropriate dosages can be determined in field trials; generally, dosages of 10 ng to 1 μg/kg/day are sufficient to induce a desired biological effect.

EXAMPLE 1

Isolation of cDNA encoding bGM-CSF and Expression of Active Protein in COS-7 Cells A cDNA polynucleotide probe was prepared from a 550 base pair (bp) HincII/NcoI fragment of the structural sequence of a human GM-CSF cDNA by nick-translation using DNA polymerase I. This probe includes all of the open reading frame for human GM-CSF plus some 3' and 5' noncoding flanking sequences. The method employed was substantially similar to that disclosed by Maniatis et al., supra.

A cDNA library was constructed by reverse transcription of polyadenylated mRNA isolated from total RNA extracted from bovine BT2 cells. The cells were cultured in RPMI 1640 medium plus 10% fetal bovine serum for 16 hours in the presence of 5% phytohemagglutin-A (PHA-A) and 10 ng/ml phorbol myrtistate acetate (PMA) in order to elicit maximal GM-CSF specific messenger RNA production. The cDNA was rendered double-stranded using DNA polymerase I, blunt-ended with T4 DNA polymerase, methylated with EcoRI methylase to protect EcoRI cleavage sites within the cDNA, and ligated to EcoRI linkers. The resulting constructs were digested with EcoRI to remove all but one copy of the linkers at each end of the cDNA, and ligated to EcoRI-cut and dephosphorylated arms of bacteriophage λgt10 (Huynh et al., *DNA Cloning: A Practical Approach*, Glover, ed., IRL Press, pp. 49-78). The ligated DNA was packaged into phage particles using a commercially available kit to generate a library of recombinants (Stratagene Cloning Systems, San Diego, CA, USA 92121). Recombinants were plated on *E. coli* strain C600(hfl−) and screened by standard plaque hybridization techniques under conditions of moderate stringency (60° C., 6xSSC). In screening approximately 100,000 plaques, four clones were isolated from the library which hybridized to the cDNA probe. The clones were plaque purified and used to prepare bacteriophage DNA which was digested with EcoRI. The digests were electrophoresed on an agarose gel, blotted onto nylon filters, and retested for hybridization. The clones were digested with EcoRI and subcloned into an EcoRI-cut derivative (pGEMBL) of the standard cloning vector pBR322 containing a polylinker having a unique EcoRI site, a BamH1 site and numerous other unique restriction sites. An exemplary vector of this type is described by Dente et al., *Nucleic Acids Research* 11:1645 (1983). Restriction mapping indicated the presence of an insert of approximately 800 bp in one of the clones. This insert was subcloned and sequenced. Clone bGM-CSF 4.7 contained a DNA segment including an open reading frame encoding a protein of 143 amino acids having a predicted molecular weight of 16.2 kilodaltons (Kd) and bearing approximately 71% homology to human GM-CSF and 52% homology to murine GM-CSF.

A eukaryotic high expression vector (HiXP) was assembled from SV40, adenovirus 2, and pBR322 DNA comprising, in sequence: (1) an SV40 fragment containing the origin of replication, early and late promoters, and enhancer; (2) an adenovirus 2 fragment containing the major late promoter, the first exon and part of the first intron of the tripartite late leader; (3) a synthetic sequence comprising a HindIII site; a splice acceptor site, the second and third exons of the adenovirus 2 tripartite leader and a multiple cloning site; (4) additional SV40 sequences containing early and late polyadenylation sites; (5) adenovirus 2 sequences including the virus-associated RNA genes; and (6) pBR322 elements for replication in *E. coli*.

A 470 bp EcoRI/HindIII fragment of bGM-CSF clone 4.7 was inserted into the HiXP multiple cloning site to yield a HiXP expression vector for bGM-CSF. This vector and a control vector with no insert were transfected into monkey COS-7 cells using DEAE-dextran followed by chloroquine treatment, as disclosed by Luthman et al., *Nucleic Acids Res.* 11:1295 (1983) and McCutchan et al., *J. Natn. Cancer Inst.* 41:351 (1968). The cells were then grown in culture for three days to permit transient expression of the inserted sequence. Cell culture supernatants were assayed in triplicate for GM-CSF activity using a bovine bone marrow proliferation assay as described elsewhere in the specification. Supernatants of control cultures exhibited no detectable biological activity in the assay, while supernatants of cells transfected with the HiXP/bGM-CSF plasmid contained an average of 648 units/ml GM-CSF activity. SDS-PAGE indicated the presence of a 22 Kd protein in the bGM-CSF-transfected COS-7 supernatants which did not appear in the supernatants of the control cultures.

EXAMPLE 2

Expression of bGM-CSF in a Yeast System

To express bGM-CSF as a secreted fusion protein in yeast, a 510 bp fragment containing the coding region of the bGM-CSF gene was isolated from bGM-CSF cDNA clone 4.7 by cleavage with BamHI and Sau3A. The fragment was inserted into BamH1-cut pBC120, a derivative of pα3, which is a yeast plasmid deposited as ATCC 53220. pBC120 includes (1) an origin of replication and Ap$^r$ gene from pBR322 enabling selection and replication in *E. coli*; (2) the TRP1 gene and 2μ origin of replication for selection and replication in *S. cervisiae*; (3) the yeast alcohol dehydrogenase 2 (ADH2) promoter followed by the yeast pre-pro α-factor leader sequence to allow foreign protein expression and secretion from yeast; (4) a sequence encoding the N-terminal epitope or identification leader Asp-Tyr-Lys-(Asp$_4$)-Lys ("flag") fused adjacent to and in-frame with the α-factor leader sequence; and (5) an origin of replication for the single stranded bacteriophage f1, derived from the pEMBL vector described by Dente et al., *Nucleic Acids Research* 11:1645 (1983), which allows production of single stranded DNA copies of the plasmid in appropriate strains of *E. coli*.

The resulting plasmid, pBC158, contains the following sequence:

```
     (KpnI)
      Pro  Leu  Asp  Lys  Arg  Asp  Tyr  Lys  Asp
   ←G GTA  CCT  TTG  GAT  AAA  AGA  GAC  TAC  AAG
   ←C CAT  GGA  AAC  CTA  TTT  TCY  CTG  ATG  TTC
      Asp  Asp  Asp  Lys  ----------------------------------
      GAC  GAC  GAT  GAC ⎡AAG  AGG  CCT  CCA  TGG
      CTG  CTG  CTA  CTG ⎣TTC  TCC  GGA  GGT  ACC
   ------------------------(BamH1)------------------------
      ATC  CCC  GGG  TAC  CGA  CCT  CGA  ATT  CCG
      TAG  GGG  CCC  ATC  GCT  CGA  GCT  TAA  GGC
      ---------------------------------- Ala  Pro  Thr
      GGC  AGC  TTC  TCC  CC⎤ GCA  CCT  ACT
      CCG  TCG  AAG  AGG  GG⎦ CG   GGA  TGA

Arg---------(bGM-CSF)-------------→
      CGC-----------------------------→
      GCG-----------------------------→
```

In order to delete the 53 bp sequence (bracketed above) between segments encoding the identification leader and mature bGM-CSF, in vitro mutagenesis was conducted by a method similar to that described by Walder and Walder, *Gene* 42:133 (1986), as follows.

Single-stranded DNA was generated by transforming *E. coli* strain JM107 and superinfecting with helper phage IR1. Single-stranded DNA was isolated and annealed to a mutagenic oligonucleotide having the sequence 5'-GACGATGACAAGGCACCTACTCGC-3', which effectively deletes the intervening undesired sequence. Annealing and yeast transformation conditions were substantially similar to those disclosed by Walder and Walder, supra. Yeast transformants were selected by growth on medium lacking tryptophan, pooled, and DNA extracted substantially as described by Holm et al., *Gene* 42:169 (1986). This DNA, containing a mixture of wild-type and mutant plasmid DNA, was used to transform *E. coli* RR1 to ampicillin resistance. The resulting colonies were screened by hybridization to a radiolabelled sample of the foregoing mutagenic oligonucleotide under stringent conditions (e.g., 55° C., 6xSSC). Hybridizing colonies were then selected, and plasmid DNA (pBC159) purified and restriction mapped to verify plasmid construction.

Purified plasmid DNA was then employed to transform a diploid yeast strain of *S. cerevisiae* (XV2181) by standard techniques, such as those disclosed in EPA 0165654, selecting for tryptophan prototrophs. The resulting transformants were cultured for expression of a flag-bGM-CSF fusion protein. Cultures to be assayed for biological activity were grown in 20–50 ml of YPD medium (1% yeast extract, 2% peptone, 1% glucose) at 37° C. to a cell density of $1-5 \times 10^8$ cells-ml. Cells were then removed by centrifugation and the medium was filtered through a 0.45μ cellulose acetate filter. Supernatants produced by the transformed yeast strain were then assayed by reaction with a mouse monoclonal antibody followed by horseradish peroxidase conjugated goat anti-mouse antibody to detect the presence of the flag peptide, and also assayed in a bovine bone marrow proliferation assay for GM-CSF activity, which confirmed expression of a biologically active protein.

What is claimed is:

1. An isolated DNA segment encoding bovine granulocyte-macrophage colony stimulating factor (bGM-CSF).

2. An isolated DNA segment according to claim 1 encoding amino acids 18-143 of the polypeptide sequence depicted in FIG. 2.

3. A recombinant expression vector comprising a DNA segment according to claim 2.

4. A recombinant expression system comprising a vector according to claim 3 and an appropriate host cell.

5. A process for preparing purified recombinant bovine GM-CSF, comprising culturing a recombinant expression system according to claim 4 under conditions promoting expression.

6. A recombinant expression vector comprising a DNA segment according to claim 1.

7. An isolated DNA segment according to claim 1, comprising the sequence of nucleotides 52-429 depicted in FIG. 2.

8. A recombinant expression vector comprising a DNA segment according to claim 7.

9. A recombinant expression system comprising a vector according to claim 8 and an appropriate host cell.

10. A process for preparing purified recombinant bovine GM-CSF, comprising culturing a recombinant expression system according to claim 9 under conditions promoting expression.

* * * * *